United States Patent [19]

Lehnert et al.

[11] Patent Number: 5,119,668

[45] Date of Patent: Jun. 9, 1992

[54] APPARATUSES AND METHODS FOR INCORPORATING BLOWING AGENTS INTO LIQUIDS FOR THE PRODUCTION OF POLYMER FOAMS AND FOR MEASURING THE VOLUMETRIC EXPANSION POTENTIAL OF MIXTURES THEREOF

[75] Inventors: Andrew B. Lehnert, Copley, Ohio; Henri J. M. Gruenbauer, HC Oostburg, Netherlands

[73] Assignee: The Dow Chemical Company, Midland, Mich.

[21] Appl. No.: 558,086

[22] Filed: Jul. 24, 1990

[51] Int. Cl.$^5$ .................. G01N 7/00; G01N 33/44
[52] U.S. Cl. .......................... 73/19.1; 73/38; 521/133
[58] Field of Search ............ 73/38, 866, 53, 19.1; 521/133

[56] References Cited

U.S. PATENT DOCUMENTS

| | | | |
|---|---|---|---|
| 3,063,952 | 9/1958 | Vieli | 260/2.5 |
| 3,096,001 | 3/1959 | Boe et al. | 222/135 |
| 3,170,972 | 1/1961 | Knipp et al. | 264/176 |
| 3,188,296 | 3/1963 | Hoppe et al. | 260/2.5 |
| 3,488,300 | 1/1970 | Burkholder et al. | 260/2.5 |
| 3,769,232 | 4/1971 | Houldridge | 252/359 |
| 3,882,052 | 5/1975 | Raynor et al. | 260/2.5 BD |
| 3,984,510 | 10/1976 | Chandra et al. | 264/40 |
| 4,089,206 | 5/1978 | Raffel et al. | 73/19 |
| 4,090,695 | 5/1978 | Stone et al. | 366/76 |
| 4,157,427 | 6/1979 | Ferber | 521/133 |
| 4,299,794 | 11/1981 | Kelley et al. | 422/68 |
| 4,329,869 | 5/1982 | Toda | 73/19 |
| 4,365,505 | 12/1982 | Hölzl | 73/19.1 |
| 4,376,172 | 3/1983 | Belangee et al. | 521/133 |
| 4,448,902 | 5/1984 | Coblenz et al. | 521/99 |
| 4,526,907 | 7/1985 | Thiele et al. | 521/133 |
| 4,565,085 | 1/1986 | Gigic et al. | 73/19.1 |
| 4,764,536 | 8/1988 | Proksa et al. | 521/50 |
| 4,862,729 | 9/1989 | Toda et al. | 73/19 |
| 4,906,672 | 3/1990 | Stone et al. | 521/130 |

FOREIGN PATENT DOCUMENTS

| | | | |
|---|---|---|---|
| 125541 | 11/1984 | European Pat. Off. | |
| 260273 | 5/1970 | U.S.S.R. | 73/38 |
| 1337770 | 9/1987 | U.S.S.R. | 73/866 |

Primary Examiner—Hezron E. Williams
Assistant Examiner—Joseph W. Roskos
Attorney, Agent, or Firm—Renner, Kenner, Greive, Bobak, Taylor & Weber

[57] ABSTRACT

Apparatus (10) for incorporating blowing agents into a liquid material provides a high pressure liquid storage and mixing tank (20) containing a mixture of liquid material (M) under pressure; means for delivering (59) a pre-determined quantity of at least one blowing agent into the mixture in minute bubbles having an average diameter of from about less than 0.5 micron up to about 100 microns; and means for uniformly distributing (60) the blowing agent throughout the liquid material. Apparatus (100) for measuring the volumetric expansion potential of a mixture of blowing agent and liquid material is also provided. It includes a high pressure liquid storage and mixing tank (106) containing a mixture of liquid material (M) and at least one blowing agent under pressure; first and second chambers (140, 141) communicating with each other and with the tank; first and second means for transferring (142, 143) the mixture into and out of the first and second chambers; and first and second means for measuring (144, 145) the volumes displaced by the mixture in the first and second chambers, wherein the second measuring chamber has a volume at least one order of magnitude greater than the first chamber. Finally methods are provided for use of the foregoing apparatuses.

30 Claims, 2 Drawing Sheets

APPARATUSES AND METHODS FOR INCORPORATING BLOWING AGENTS INTO LIQUIDS FOR THE PRODUCTION OF POLYMER FOAMS AND FOR MEASURING THE VOLUMETRIC EXPANSION POTENTIAL OF MIXTURES THEREOF

TECHNICAL FIELD

This invention relates to an apparatus and methods to incorporate blowing agents into liquid materials for the manufacture of polymer foams. More particularly, the invention related to the introduction of blowing agents as minute bubbles for the purpose of being able to prepare microcellular polymeric products. This invention also relates to an apparatus and method for determining volumetric expansion potential of a mixture of blowing agent and liquid materials and means of measuring the density and solubility thereof.

BACKGROUND OF THE INVENTION

In the manufacture of polymeric foams such as, for example, polyurethanes, polyureas, polystyrene, polyethylene and the like a heat activated blowing agent is employed to provide the desired cell structure. While it has been customary to employ a chlorinated fluorocarbon (CFC) for this purpose, the cumulative effect on the ozone layer of the atmosphere has made it desirable to utilize non-ozone depleting blowing agents. Although other gases including carbon dioxide, nitrogen, helium, ammonia, pentane, acetylene, the inert gases, air and mixtures thereof have been investigated, generally none has produced the desired cell size, structure and insulative properties obtained with the CFC's.

In the production of polyurethanes the blowing agent is mixed with a liquid monomer, or reaction component of a two part system, e.g. polyahl or isocyanate, prior to polymerization. One of the problems associated with the use of non-CFC blowing agents has been their introduction, dispersion and distribution into the liquid monomer. For a given cell structure it is known that a specific volume of blowing agent must be present however, the solubility and miscibility of the agent is an important factor with which the manufacturer must reckon.

Another problem has been the accurate determination of the volume of blowing agent actually incorporated into the liquid monomer component prior to polymerization because escape of the agent during measurement leads to erroneous determinations and, in turn, the use of incorrect amounts of the agent as corrections are made or not made.

To date the patent art provides numerous examples of apparatus and methods for using various non-CFC blowing agents in liquid monomer components. For example, the introduction of an inert gas, such as nitrogen, into a liquid reaction component of a reaction injection molding (RIM) system is taught by U.S. Pat. No. 4,157,427. In general, the gas is added to one of the precursors of a polyurethane by use of a sparger stone through which the gas is forced, under pressure. The sparger is described as a suitably sized and shaped porous rigid structure, to produce minute bubbles for better mixing, that is placed in a pipe through which the reactive component is circulated from the supply tank and then sent either to a mixing head or back to the supply tank.

U.S. Pat. No. 4,376,172 is directed toward a closed loop apparatus for controlling the addition of a gas to a liquid, such as a polyurethane precursor, in a RIM process. Additionally, means are provided for accurately measuring the amount of the gas that is added. The blowing agent or gas is added by means of a sparger which is in a stream of the reactant being recirculated from the supply tank and back to the supply tank.

Measurement of the amount of gas added to the polyurethane reactant is performed by tapping a volume of the gas-reactant mixture and holding it in a cylinder. A piston is then driven into the cylinder to check, by means of compressibility, the amount of gas which has been added.

U.S. Pat. No. 4,526,907 is directed toward a process and device for charging gas into at least one of the components combined to produce plastic foams. The reactant from one supply tank is piped through a circulation line which has a zone of compression that is higher in pressure than that in the supply tank. In this compression zone the foaming gas is added, and the mixture is subsequently forced through a throttle element to reduce the pressure before return to the supply tank. The patent also teaches that several different methods can be employed to determine the amount of gas in the gas-reactant mixture including density, partial pressure, the absorption of a beam of light, compressibility and solubility, but does not necessarily discuss means for doing so.

U.S. Pat. No. 4,906,672 is directed toward a method for the continuous manufacture of polyurethane foam. More particularly, it deals with the addition of carbon dioxide to polyurethane-forming reactants as the blowing agent and teaches that the carbon dioxide is to be dissolved into one of the reactants well before being sent to the mixing head.

Introduction is performed under high pressure, preferably 75 to 900 psig (0.57 to 6.2 MPa), in a pipe, a sufficient distance from the mixing head that uniform entrainment is achieved upon traveling from the sight of impingement to the mixing head. Once the mixture reaches the mixing head, a nozzle or series of nozzles are employed to expand the carbon dioxide-reactant mixture; however, the patent teaches that the entrainment of bubbles is to be avoided.

Finally, European Pat. No. 125,541-B discloses a device for measuring the gas charging of a liquid component used for producing synthetic plastic foam such a polyurethanes. It employs a measuring vessel, for receipt of a liquid sample periodically, and which communicates with an overflow vessel. By allowing the pressure in the measuring vessel to decrease to atmospheric, the gas laden component expands and overflows vessel which allows density to be determined.

Thus, it should be apparent that although others have employed low boiling compounds, such as, carbon dioxide, nitrogen and the like as blowing agents for polyurethane foam, apparatus and method have not been taught for the incorporation of a blowing agent in a liquid monomer, in precise amounts and bubble sizes so as to control the cell structure of the resulting foam, or for the precise measurement of the density of a mixture of blowing agent and liquid monomer, the liquefaction and solubility of the blowing agent in the mixture, or the determination of its volumetric expansion potential therefrom. Moreover, previous apparatus and methods have not been successful in providing uniform distribution of the blowing agent in the liquid monomer component, which has grossly affected the quality of the resulting foam product.

SUMMARY OF THE INVENTION

It is therefore an object of the present invention to provide an apparatus for the incorporation of blowing agents into a liquid material for the production of polymer foams.

It is another object for the present invention to provide a method for the incorporation of blowing agents into a liquid material for the production of polymer foams.

It is another object of the present invention to provide apparatus for precisely measuring the volumetric expansion potential of a mixture of a blowing agent and liquid material for the production of polymer foams.

It is still another object of the present invention to provide a method for precisely measuring the volumetric expansion potential of a mixture of a blowing agent and liquid material for the production of polymer foams.

At least one or more of the foregoing objects, together with the advantages thereof over known methods and apparatus relating to the use of blowing agents in the production of polymer foam, which shall become apparent from the specification which follows, are accomplished by the invention as hereinafter described and claimed.

In general the present application provides an apparatus for incorporating blowing agents into a liquid material comprising a high pressure liquid storage and mixing tank containing a liquid material under pressure; means for delivering a predetermined quantity of at least one blowing agent into the liquid monomer in minute bubbles having an average diameter of from about less than 0.5 micron up to about 100 microns; and means for uniformly distributing the blowing agent throughout the liquid material.

Additionally an apparatus is provided for measuring the volumetric expansion potential of a mixture of blowing agent in a liquid material component comprising a high pressure liquid storage and mixing tank containing liquid material and at least one blowing agent under pressure; first and second chambers communicating with each other and with the tank; first and second means for transferring the liquid material and blowing agent into and out of the first and second chambers; and first and second means for measuring the volumes displaced by the liquid material and blowing agent in the first and second chambers, wherein the second measuring chamber has a volume of at least one order of magnitude greater than the first chamber.

The present invention also provides a method for the incorporation of blowing agents into a liquid material comprising the steps of feeding a predetermined amount of liquid material to a supply tank; supplying a predetermined volume of at least one blowing agent to a cylinder for injection into said supply tank; pressuring the blowing agent in said cylinder; delivering the blowing agent from the cylinder to the supply tank through means located in the tank to produce bubbles in the liquid material having an average diameter of from about less than 0.5 micron up to about 100 microns.

Also provided is a method for measuring the volumetric expansion potential of a mixture of at least one blowing agent and a liquid material comprising the steps of withdrawing a quantity of the mixture from a supply tank; feeding the quantity into a first chamber under pressure; discharging the quantity from the first chamber directly into a second chamber having a volume of at least one order of magnitude greater than the first chamber whereby the blowing agent will come out of the mixture; and thereafter measuring the density of the liquid material.

Finally, the present invention provides an apparatus for incorporating blowing agents into a liquid material and measuring the volumetric expansion potential of a mixture thereof comprising a high pressure liquid storage and mixing tank containing a liquid material under pressure; means for delivering a predetermined quantity of at least one blowing agent into the liquid material in minute bubbles having an average diameter of from about less than 0.5 micron up to about 100 microns; means for uniformly distributing the blowing agent throughout the liquid material; first and second chambers communicating with each other and with the tank; first and second means for transferring the liquid material and blowing agent into and out of the first and second chambers; and first and second means for measuring the volumes displaced by the liquid material and blowing agent in the first and second chambers, wherein the second measuring chamber has a volume of at least one order of magnitude greater than the first chamber.

The volumetric expansion potential of the mixture under pressure in the supply tank can be determined from the density of the mixture under pressure in the supply tank, as determined by measuring the volumes of the first and second chambers before and after discharging and expansion, respectively. Optionally, measurement of gas loading, liquefaction and solubility of the blowing agent in the liquid material can be carried out by expanding the volume of the second measuring chamber to any desired lesser extent than is required to separate essentially all blowing agent from the mixture.

PREFERRED EMBODIMENT FOR CARRYING OUT THE INVENTION

Figure 1:
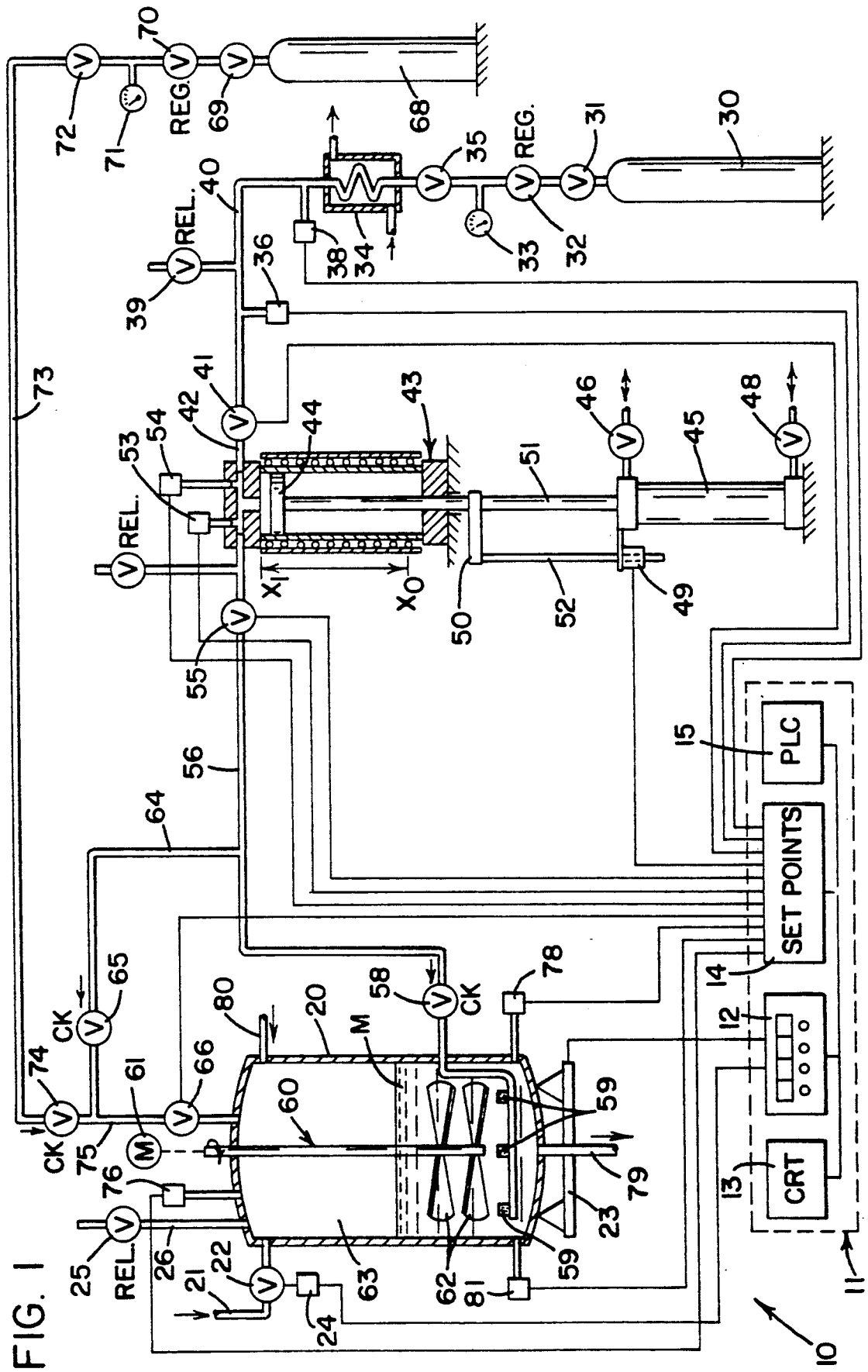
FIG. 1 is a schematic flow diagram of apparatus, according to the present invention, for incorporation of blowing agents into a liquid material employed for the manufacture of polymer foams.

The present invention is related generally to the use of a non-CFC gas e.g., carbon dioxide, nitrogen, helium, air and the like, as well as mixtures thereof and, in particular, carbon dioxide or a mixture of carbon dioxide and a noble gas such as helium, as the blowing agent for liquid monomer components of reaction mixtures. In the manufacture of polyurethane foam as a preferred example, two liquid materials, a polyol component and an isocyanate component, are prepared separately and then combined in a mixer. The reaction is quick and the mixture is injected into a suitable vessel or mold where foaming and expansion occurs and the product is actually formed. Such a process, is well known as reaction injection molding, or RIM.

In the manufacture of foam products for use as insulation, chlorinated fluorocarbons (CFC's) specifically FREON ® have been employed as the blowing agent because a very small and uniform cell structure results in the product and, in turn, an improved K factor. In order to eliminate the use of such CFC's other blowing agents such as carbon dioxide have been considered. Unfortunately, the mere addition of carbon dioxide is difficult and heretofore has often not resulted in the manufacture of quality foam products.

The invention which follows describes the addition of a non-CFC blowing agent, such as carbon dioxide, to the polyol component of a polyurethane composition although it could as readily be employed with the isocyanate component or both. Addition of the blowing agent is precisely controlled to incorporate the proper size bubbles and the amount of blowing agent necessary to provide the desired properties of the foam, including density and cell structure.

The term blowing agent is understood to include any gases and liquids which are capable of performing in substantially the same manner as the preferred blowing agent described herein for the production of polymer foams, including but not limited to compounds such as chlorofluorocarbons (CFC's), hydrochlorofluorocarbons (HFC's), hydroflouroalkanes (HFA's), hydrocarbons, esters, ethers, noble gases, ammonia, pentane, and mixtures thereof, as well as water and steam, and particularly carbon dioxide, helium, nitrogen and air. As will be appreciated by those skilled in the art, a single blowing agent or mixture of agents can be employed. Carbon dioxide may be selected because of its relative convenience in handling. It may also be employed in admixture with a noble gas, such as helium, as will be appreciated by those skilled in the art.

The term liquid material is understood to include any liquid monomer that can be converted into a polymer by a polymerization reaction. Of particular interest are polyurethane, polyurea and polyisocyanurate polymers which are produced by contacting under reactive conditions suitable amount of liquid material comprising a polyahl and a polyisocyanate.

The term polyahl is understood to include any compound containing active hydrogens in the sense of the Zerewitinoff test, see Kohler, Journal of the American Chemical Society page 381, Volume 49 (1927). Representative active-hydrogen groups include —OH, —COOH, —SH and —NHR where R is H, alkyl, aryl and the like.

The term isocyanate is understood to include organic isocyanates useful in making polyurethanes, polyureas and polyisocyanurates, such as, aromatic, aliphatic and cycloaliphatic polyisocyanates. Exemplary compounds include toluene diisocyanate, diphenylmethane diisocyanate and mixtures thereof.

A crude polyisocyanate may also be used in the practice of this invention, such as, the crude toluene diisocyanate obtained by the phosgenation of a mixture of toluene diamines or the crude diphenylmethane diisocyanate obtained by the phosgenation of crude methylene diphenyhlamine. The preferred undistilled or crude polyisocyanates are disclosed in U.S. Pat. No. 3,215,652, incorporated herein by reference. Derivatives of the above identified isocyanates, such as, prepolymers, are equally suitable for use in the present invention.

In addition, other liquid materials include molten thermoplastic resins such as polystyrene, polyethylene and the like which are customarily mixed with various blowing agents to produce foam products. The production of such polymer foams is disclosed in U.S. Pat. Nos. 4,344,710 and 4,470,938, the subject matter of which is incorporated herein by reference. Thus, liquid materials refers to monomers as well as polymers and should be thought of broadly as liquid, polymer foam forming components.

Introduction of the blowing agent generally gives rise to a number of different types of phase behavior which depend on the miscibility characteristics of the blowing agent/liquid material combination at the given temperature and pressure. Insoluble blowing agents under high pressure, may give rise to the presence of both droplets of liquid blowing agent and bubbles of gaseous blowing agent in the liquid material, provided the temperature of the system remains below the critical temperature of the blowing agent and the pressure is high enough to cause liquefaction. Under similar conditions, a mixture of a soluble blowing agent and the liquid material will contain single, dissolved blowing agent molecules in addition to distinct droplets and bubbles of liquified and gaseous blowing agent, respectively.

The blowing agent or mixture of agents are incorporated into the liquid material forming a mixture thereof. Owing to the different phases and types of mixtures possible, the term "incorporation" as used herein includes mixtures of soluble as well as insoluble blowing agents with liquid material, which are dissolved and distributed or disbursed, respectively. Hence, the term mixture can include combinations of an insoluble blowing agent with a liquid material as well as solutions of a soluble blowing agent in a liquid material. It should also be appreciated that liquid and gas blowing agents can be employed and thus, incorporation includes liquid and gas bubbles and molecules as well as droplets. Pressure conditions can also affect liquefaction, as noted hereinabove. In all instances, the present invention provides the uniform incorporation of the blowing agent in the liquid material.

The prior art teaches determination of volumetric expansion potential by measuring gas loading using measured density of the blowing agent/liquid material mixture at actual operating pressure (U.S. Pat. No. 4,157,427) or at ambient pressure. To this purpose, mixtures of polyols and blowing agents are expanded either from a preset operating pressure to a second, lower set pressure (U.S. Pat. No. 4,376,172) or from a given preset operating pressure to atmospheric pressure (European Pat. No. 125,541-B), However, it should be clear from the above discussion that these methods will provide erroneous results where liquid blowing agent droplets and/or dissolved single blowing agent molecules remain in the liquid material after expansion. In such instances, relatively correct gas loading may be obtained but, the relationship between gas loading and density of the expanded product will be in error to the extent that expansion potential is not accounted for by the density measurement.

Usage of the present invention will enable one to expand mixtures of blowing agent and liquid material selectively so as to ensure complete evaporation of all blowing agent present in the mixture. In this way, the correct assessment of final densities of the expanded products can be made, irrespective of the properties and composition of the blowing agent/liquid material combination considered. It is believed that this feature will be unique and highly beneficial to employ new non-ozone depleting blowing agent compositions for a plurality of expanded polyurethane products. Optionally, the invention also enables one to expand such mixtures to any desired final pressure, thus allowing for measurement of both solubility and gas loading of the blowing agent in the mixture.

With respect now to the drawings, apparatus, indicated generally by the numeral 10, is depicted in FIG. 1. Apparatus 10 includes approximately one-half of a two component liquid monomer system, e.g., polyol and isocyanate, for the manufacture of polyurethane. For purposes of discussion, apparatus 10 shall be described in conjunction with the polyol liquid monomer component.

Apparatus 10 provides an operator panel 11, housing a digital indicator module 12, a video display monitor (CRT) 13, a set point panel 14 with various set point control keys for setting points and a programmable logic controller (PLC) 15. As is known in the art, the operator panel is connected to a plurality of valves and transducers for operation of the component elements of apparatus 10 which shall be described next.

A liquid monomer holding and mixing tank 20 is provided for receipt of a supply of monomer M. Tank 20 is designed to withstand pressures of up to about 1000 psig (6.9 MPa) and is fed via conduit 21, through valve 22 a supply of liquid monomer from a source (not shown). Preferably the pressure within the monomer tank may be about 600 psig (4.1 MPa) and most preferably about 435 psig (3.0 MPa). Nevertheless, it is to be understood that even higher pressures are not to be precluded, if a desired monomer and blowing agent combination may someday require such pressure, and similarly, pressures as low as 70 psig (0.5 MPa) may be suitable with other combinations. Monomer M is fed at room temperature and has a specific gravity of from about 1.02 to 1.2, although these parameters do not constitute a limitation on the present invention.

Tank 20 is positioned over a load cell 23 so that a pre-determined amount of monomer M selected by the digital indicator module 12 is delivered. Upon reaching the prescribed weight, a signal from the module 12 will energize the solenoid 24 to close valve 22. A relief valve 25 is provided to vent air via conduit 26 while the tank 20 is filled. The weight of liquid monomer M is now read from indicator module 12.

As noted hereinabove, an object of the present invention is to substitute an alternative blowing agent, such as carbon dioxide, for CFC's normally employed. Hence, a supply tank 30 is provided for the delivery of gas via exit valve 31, pressure regulator 32, pressure gage 33, and heater 34, controlled by valve 35. Temperature and pressure of the gas are measured by transducers 36, 38 and indicated on the CRT 13, with excess pressure being relieved through valve 39 in conduit 40.

Blowing agent is fed through control valve 41 and conduit 42 into a delivery cylinder 43 which contains a piston 44. Piston 44 is, in turn, driven by an hydraulic cylinder 45, located in tandem with cylinder 43. Speed and movement thereof are controlled by valves 46 and 48. Because the area of the piston 44 and cylinder 43 are constant, it is only necessary to establish the distance of piston travel between points X and $X_1$ to establish a pre-determined volume of blowing agent.

Based upon the percent of blowing agent required to produce the expanded product, typically ranging from about two to 30 percent by weight, the volume of the blowing agent to be fed into cylinder 43 is calculated and the set points $X_0$ and $X_1$ are displayed on the CRT 13.

A position transducer 49 is employed to provide electronic feedback as to the position of piston 44. As depicted in the drawing, an arm 50 is carried by the piston rod 51 from cylinder 45 which, in turn, positions a linear position transducer rod 52 for precisely determining the location of piston 44. When the piston 44 is at position $X_1$ a signal is given to stop the stroke.

The inlet valve 41 is opened and the piston 44 is retracted to the position $X_0$, filling the cylinder 43 with the correct amount of blowing agent until pressure and temperature transducers 53 and 54 respectively, indicate the correct operating parameters, from about 70 psig (0.5 MPa) to about 1000 psig (6.9 MPa) with about 435 psig (3.0 MPa) being preferred and a temperature of from about 60° to 180° F. (16° to 86° C.), with about 110° F. (44° C.) being preferred.

The piston 44 is now urged from position $X_0$ to $X_1$ to compress and deliver the gas through exit valve 55 and conduit 56, over check valve 58 and through a series of sparger stones 59 located near the bottom of tank 20. The sparger stones are of a porosity to create minute gas bubbles or droplets having an average diameter of up to about 100 microns, preferably about 10 microns, more preferably 1 micron and most preferably 0.5 micron. Orientation of the sparger stones 59 is horizontal, rather than vertical, to cover a large area of the tank 20.

After introduction of the blowing agent, it is important that the liquid monomer be mixed thoroughly to keep the blowing agent uniformly incorporated. An agitator 60 driven by motor 61 provides dual blades 62 to maintain distribution of the blowing agent. At this stage, the combined weight of the monomer and blowing agent can be checked and if additional amounts are necessary, the foregoing sequence of steps may be repeated.

Because one element of the process is high pressure introduction of blowing agent, it may be necessary to fill the vapor space 63 above the monomer in tank 20 with additional gas, such as carbon dioxide or nitrogen. This can be accomplished by directing the gas from tank 30 through conduit 64, check valve 65 and inlet valve 66. If nitrogen is desired as a blanketing gas, it can be fed from a source 68 through exit valve 69, regulator 70, pressure gage 71, control valve 72, conduit 73 and check valve 74 into conduit 75.

The correct blanket pressure is indicated by pressure transducer 76 and once the total liquid and blanket pressure have been indicated from a signal of the pressure transducer 78, the polyol is now circulated out conduit 79 by a pump (not shown) and through a heat exchanger (not shown) and returned to the tank via conduit 80. The operating temperature is indicated from a signal of temperature transducer 81.

When both polyol and polyisocyanate are ready for reaction, monomer M (polyol) is directed out of the tank via conduit 79 for reaction with the polyisocyanate in a mixhead (not shown).

Figure 2:
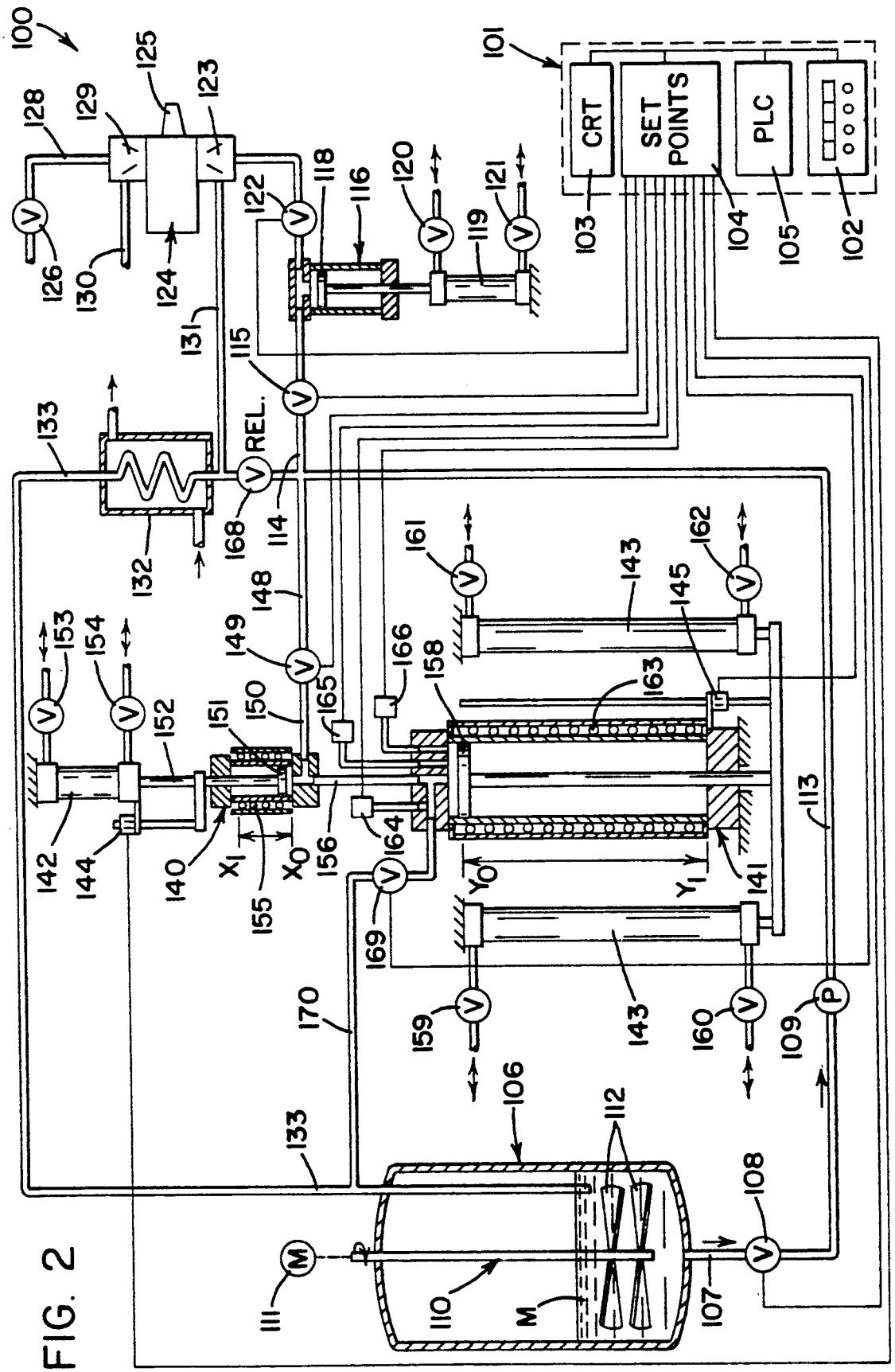
FIG. 2 is a schematic flow diagram of apparatus, according to the present invention, for measuring volume expansion, density, and solubility of a blowing agent in a liquid material employed for the production of polymer foams.

The present invention provides that the control and measurement of the percent of gas loading in the liquid monomer will correlate the data from the system with standard temperature and pressure. With reference to FIG. 2, the apparatus indicated generally by the numeral 100 shall be described next. For simplicity again, only one of the two monomer streams has been depicted.

Apparatus 100 includes an operator panel 101 which houses a digital indicator module 102, a CRT 103, set point panel 104 and PLC 105. It provides a liquid monomer tank 106, similar to tank 20 in FIG. 1, which is designed for pressures up to about 1000 psig (6.9 MPa). Tank 106 contains a quantity of liquid monomer M, from a source (not shown), and is also supplied with a blowing agent.

Again, in the interest of simplicity, the related structure for introduction of the blowing agent, such as depicted in FIG. 1, has not been shown although it is to be understood that the present apparatus for the measurement of volumetric expansion potential can be employed in conjunction with the apparatus 100 or, it can be employed with other blowing agent/liquid monomer mixtures produced as known in the art.

The liquid monomer is withdrawn from a conduit 107 at the base of the tank 106, through an air operated ball valve 108 and pump 109 for reaction with the second monomer component or, for measurement of the volumetric expansion potential. The monomer solution is mixed by agitator 110 driven by motor 111 and providing dual blades 112 to maintain uniform incorporation of the blowing agent.

For purposes of reaction, the monomer is fed via conduits 113 and 114, through inlet valve 115 to the inlet cylinder 116, under a pressure of between about 70 psig (0.5 MPa) and 1000 psig (6.9 MPa), preferably 435 psig (3.0 MPa), as discussed hereinabove. Cylinder 116 provides a piston 118, actuated by an hydraulic cylinder 119, equipped with hydraulic control valves 120, 121. The monomer M is drawn into cylinder 116, then valve 115 is closed and valve 122 is opened and the monomer is charged through a convergent nozzle 123 in a mixing head 124 and finally through exit chamber 125. The second reactive monomer, such as an polyisocyanate, will be simultaneously injected through valve 126 and conduit 128, convergent nozzle 129 in mixing head 124 and through exit chamber 125, thoroughly mixed with the monomer M (polyol). When the mixing head is closed, both streams will be returned to their respective tanks via conduits 130 and 131. The stream flows through heater 132 and is returned via conduit 133 to the tank 106.

The actual volumetric expansion potential measuring components include first and second measuring chambers or cylinders, 140 and 141 respectively, first and second means for the movement of blowing agent/monomer solution into and out of said first and second cylinders, 142 and 143 respectively, and first and second means for measuring the volumes displaced by said first and second cylinders during use, 144 and 145 respectively. A quantity of blowing agent/monomer is fed from tank 106 through conduit 148, valve 149 and conduit 150 and into first cylinder 140. Cylinder 140 contains a piston 151 and a piston rod 152 driven by an hydraulic cylinder, or first means for movement 142, operated by hydraulic control valves 153, 154. Means for measuring 144 comprises a linear position transducer which is controlled by keys of the set point control panel 104 to withdraw a precise volume of blowing agent/monomer. The volume of the solution is controlled as is the pressure and temperature via heating element 155 which encompasses cylinder 140. Volume and temperature ranges are the same as stated hereinabove and need not be repeated here.

The second cylinder 141 provides for blowing agent expansion control and measuring and is appropriately sized to provide an volume increase of at least one order of magnitude e.g., from about 10 times the volume of cylinder 140, and upward to two orders of magnitude or higher. This will result in a pressure drop from a high of about 1000 psig (6.9 MPa) to atmospheric or less than atmospheric pressures, i.e., a vacuum. The mixture is driven from cylinder 140, via conduit 156, into the cylinder 141 as the piston 158 is withdrawn via second means for movement 143, driven by hydraulic control valves 159-162. Cylinder 141 is also provided with heating means 163 and, the second means for measuring 145 comprises another linear position transducer. Pressure transducers 164, 165 and temperature transducer 166 are also provided and are connected to the keys of set point control panel 104.

For measurement of volumetric expansion potential, the air operated ball valve 115 is closed and pump 109 circulates the mixture over back pressure relief valve 168, heat exchanger 132 and conduit 133 to the tank 106, in order to provide precise temperature conditioning of the mixture. Once all of the conditions have been met, return valve 169 is closed and both cylinders 140 and 141 are in the closed positions, $X_0$ and $Y_0$ respectively. The piston 151 of first cylinder 140 is now moved at a controlled rate by means 142 to the $X_1$ position based upon information supplied by the PLC 105. Inasmuch as the area of the piston is constant, it is only necessary to input the distance travelled in order to obtain the volume of the mixture. A comparator in the PLC is provided to compare the actual distance travelled through a signal from the transducer 144 with the set point panel 104. Pressure and temperature from transducers 164 and 166 are also checked and compared.

The piston 151 first of cylinder 140 is now moved toward the $X_0$ position while at the same time, the piston 158 of the second, or expansion cylinder 141, is moved by means of 143 toward a position such that a volume of said mixture is transferred from the first to the second cylinder at constant pressure and temperature. In the second step, the piston 158 is moved to a position such that all the blowing agent comes out of the mixture. This position is illustrated in FIG. 2. Because the volume of the second cylinder 141 is greater by at least one order of magnitude than that of the first cylinder 140, the blowing agent in the mixture will evaporate. As noted hereinabove, the volume of the second cylinder can be as great as two orders of magnitude, or greater, than the volume of the first cylinder. The piston 158 of cylinder 141 is moved toward the $Y_1$ position until the pressure transducer 165 reads the pressure set to such a level necessary to drive all blowing agent out of the mixture. The piston 158 of cylinder 141 may be positioned to create a vacuum if required. At this time, the distance travelled will be provided through a signal from the linear position transducer 145.

Because the cross sectional area of the expansion cylinder 141 is constant, knowing the distance travelled, will provide the volume of the blowing agent in the cylinder. The density of the mixture of monomer and blowing agent under pressure in the supply tank follows from the formula:

$$Ri = \frac{1}{(Vi/Vf)[Wb(1/Rb - 1/Rm) + 1/Rm]}$$

where $Ri$ = Density of the mixture in the supply tank at operating pressure $Rm$ = Density of the monomer at final pressure after expansion has caused all blowing agent to come out of the mixture.

Rb = Density of the blowing agent at final pressure after expansion
Wb = Weight fraction of blowing agent in the mixture
Vi = Volume of the mixture at operating pressure
Vf = Volume of the mixture at final pressure after expansion has occurred Upon completion of the measurement, the piston 158 of the expansion cylinder 141 will move toward the $Y_0$ position. By opening exit valve 169 all residue will be purged over conduit 170 to the tank 106.

As should be apparent from the foregoing description, the apparatus and method for incorporating blowing agents provide a closed system in the sense that a pre-determined amount of blowing agent is delivered directly from a source, to the mixing vessel and then incorporated therein, without escape to the atmosphere. Understandably, to ensure incorporation of precise amounts of blowing agent, all conduits should be appropriately charged so that the desired blowing agent and amount thereof is actually delivered to the liquid material. In similar fashion, the apparatus and method for measuring the volumetric expansion also provide a closed system inasmuch as samples taken from the mixing vessel are tested without direct contact with the surrounding atmosphere or loss of blowing agent.

Thus it should be evident that the apparatuses and methods of the present invention provide a highly effective and accurate system for incorporating minute bubbles of at least one blowing agent into one or both liquid monomers of a two component reactive system for the manufacture of polymer foams, as well as for measuring the amount of volumetric expansion potential of a blowing agent/liquid monomer mixture. The invention is particularly suited for producing polyurethane foams and the use of low boiling blowing agents, such as, carbon dioxide not necessarily limited thereto. The apparatuses for incorporating and for measuring can be combined and used in the same overall system or, each can be used separately with other equipment, methods and the like, as well as for the manufacture of other polymer foams.

Regarding the latter, the apparatuses and methods of the present invention can also be employed separately or together with other liquid materials including molten thermoplastic resins, such as polystyrene and polyethylene, to which blowing agents are added to form polymer foams. Accordingly, while the present invention includes as the preferred embodiment a disclosure of liquid monomers, the invention is not necessarily limited thereto.

Based upon the foregoing disclosure, it should now be apparent that the use of the apparatus described herein will carry out the objects set forth hereinabove. It is, therefore, to be understood that any variations evident fall within the scope of the claimed invention and thus, the selection of specific component elements can be determined without departing from the spirit of the invention herein disclosed and described. Moreover, the scope of the invention shall include all modifications and variations that may fall within the scope of the attached claims.

We claim:

1. Apparatus for incorporating blowing agents into a liquid material comprising:
    a high pressure liquid supply and mixing tank containing a liquid material under pressure;
    means for delivering a pre-determined quantity of at least one blowing agent into said liquid material in minute bubbles having an average diameter of from about less than 0.5 micron up to about 100 microns; and
    means for uniformly distributing said blowing agent throughout said liquid material.

2. Apparatus for incorporating blowing agents, as set forth in claim 1, wherein said means for delivering includes
    cylinder means providing a movable piston;
    means for moving said piston; and
    means for controlling the position of said piston between opened and closed positions.

3. Apparatus for incorporating blowing agents, as set forth in claim 2, wherein said means for delivering further includes
    means for controlling the temperature of said blowing agents within said cylinder means; and
    transducer means for monitoring the temperature and pressure of blowing agent within said cylinder.

4. Apparatus for incorporating blowing agents, as set forth in claim 1, wherein said means for delivering further includes
    a plurality of sparger stones, located beneath the liquid material to form said bubbles of blowing agent.

5. Apparatus for incorporating blowing agents, as set forth in claim 1, wherein said means for delivering further includes
    means for monitoring the weight of said supply tank, said liquid material and said quantity of blowing agent.

6. Apparatus for incorporating blowing agents, as set forth in claim 1, wherein said bubbles of blowing agent have an average diameter of less than about 0.5 micron.

7. Apparatus for measuring the volumetric expansion potential of a mixture of blowing agent in a liquid material component comprising:
    a high pressure liquid supply and mixing tank containing liquid material and at least one blowing agent under pressure;
    first and second chambers communicating with each other and with said tank;
    first and second means for transferring said liquid material and blowing agent into and out of said first and second chambers; and
    first and second means for measuring the volumes displaced by said liquid material and blowing agent in said first and second chambers, wherein said second measuring chamber has a volume of at least one order of magnitude greater than said first chamber.

8. Apparatus for measuring the volumetric expansion potential of a mixture of blowing agent and liquid material, as set forth in claim 7, wherein said first chamber provides a piston communicating with said first means for transferring and is movable between opened and closed positions and
    said second chamber provides a piston communicating with said second means for transferring and is movable between opened and closed positions.

9. Apparatus for measuring the volumetric expansion potential in a mixture of blowing agent and liquid material, as set forth in claim 8, further comprising
    conduit means connecting said first and second chambers whereby as said piston in first chamber is moved to said closed position, said piston in said second chamber is moved to said opened position.

10. Apparatus for measuring the volumetric expansion potential of a mixture of blowing agent and liquid material, as set forth in claim 7, further including:
    means for controlling the temperature within said first and second chambers; and
    transducer means for monitoring the temperature and pressure within said second chamber.

11. Apparatus for measuring the volumetric expansion potential of a mixture of blowing agent and liquid material, as set forth in claim 7, further including
    means for circulating said mixture outside of said supply tank to establish a constant, desired temperature and pressure within said tank.

12. Apparatus for measuring the volumetric expansion potential in a mixture of blowing agent and liquid material, as set forth in claim 7, wherein said pressure ranges from at least about 70 psig (0.5 MPa) up to about 1000 psig (6.9 MPa).

13. Apparatus for measuring the volumetric expansion potential in a mixture of blowing agent and liquid material, as set forth in claim 12, wherein said pressure is about 435 psig (3.0 MPa).

14. A method for the incorporation of blowing agents into a liquid material comprising the steps of:
    feeding a pre-determined amount of liquid material to a supply tank;
    supplying a pre-determined volume of at least one blowing agent to a cylinder for injection into said supply tank;
    pressuring said blowing agent in said cylinder;
    delivering said blowing agent from said cylinder to said supply tank through means located in said tank to produce bubbles in the liquid material having an average diameter of from about less than 0.5 micron up to about 100 microns.

15. A method, as set forth in claim 14, including the additional step of
    raising the pressure in said supply tank to a range of from at least about 70 psig (0.5 MPa) up to about 1000 psig (6.9 MPa) prior to said step of delivering.

16. A method, as set forth in claim 14, wherein said means located in said tank comprises a plurality of sparger stones.

17. A method, as set forth in claim 14, including the additional steps of
    weighing said supply tank with liquid material; and
    monitoring said weight as said blowing agent is introduced.

18. A method, as set forth in claim 14, wherein said blowing agent is selected from the group consisting of gases and liquids which are capable of performing as blowing agents in the production of polymer foams and said liquid material is selected from the group consisting of monomers and polymers employed for the production of polymer foams.

19. A method, as set forth in claim 18, wherein said blowing agent comprises carbon dioxide and said liquid material is selected from the group consisting of polyahls and isocyanates.

20. A method, as set forth in claim 14, wherein said bubbles of blowing agent have an average diameter of less than about 0.5 microns.

21. A method for measuring the volumetric expansion potential of a mixture of at least one blowing agent and a liquid material comprising the steps of:
    withdrawing a quantity of said mixture from a supply tank;
    feeding said quantity into a first chamber under pressure;
    discharging said quantity from said first chamber directly into a second chamber having a volume of at least one order of magnitude greater than said first chamber whereby said blowing agent will come out of the mixture; and thereafter measuring the density of said liquid material.

22. A method, as set forth in claim 21, wherein said step of feeding includes the steps of
    withdrawing a piston in said first chamber a pre-determined distance to form a cavity therein for said quantity; and
    controlling the position of said piston between limits to define opened and closed positions of said first chamber.

23. A method, as set forth in claim 22, including the additional step of controlling the temperature of the liquid material in said first chamber.

24. A method, as set forth in claim 21, including the additional step of
    circulating said mixture outside of said supply tank to establish a constant, desired temperature and pressure.

25. A method, as set forth in claim 21, wherein said step of discharging includes the steps of
    withdrawing a piston in said second chamber a distance to form a cavity having such a pressure that the blowing agent in said mixture will come out of said mixture; and
    controlling the position of said piston between limits to define opened and closed positions of said second chamber.

26. A method, as set forth in claim 21, wherein the pressure on said liquid material/blowing agent mixture in said tank and said first chamber ranges from at least about 70 psig (0.5 MPa) up to about 1000 psig (6.9 MPa) and the pressure in said second chamber can be varied from about 1000 psig (6.9 MPa) to less than atmospheric, depending on the liquid material/blowing agent mixture being measured.

27. A method, as set forth in claim 26, herein said pressure in said tank is about 435 psig (3.0 MPa).

28. A method, as set forth in claim 21, wherein said blowing agent is selected from the group consisting of gases and liquids which are capable of performing as blowing agents in the production of polymer foams and said liquid material is selected from the group consisting of monomers and polymers employed for the production of polymer foams.

29. A method, as set forth in claim 28, wherein said blowing agent comprises carbon dioxide and said liquid material is selected from the group consisting of polyahls and isocyanates.

30. Apparatus for incorporating blowing agents into a liquid material and measuring the volumetric expansion potential of a mixture thereof comprising:
    a high pressure liquid supply and mixing tank containing a liquid material under pressure;
    means for delivering a pre-determined quantity of at least one blowing agent into said liquid material in minute bubbles having an average diameter of from about less than 0.5 micron up to about 100 microns;
    means for uniformly distributing said blowing agent throughout said liquid material;
    first and second chambers communicating with each other and with said tank;

first and second means for transferring said liquid material and blowing agent into and out of said first and second chambers; and first and second means for measuring the volumes displaced by said liquid material and blowing agent in said first and second chambers, wherein said second measuring chamber has a volume of at least one order of magnitude greater than said first chamber.

* * * * *